United States Patent
Henry et al.

(10) Patent No.: US 8,939,147 B2
(45) Date of Patent: Jan. 27, 2015

(54) IDENTIFICATION SYSTEM AND METHOD FOR MASK AND VENTILATOR COMPONENTS

(75) Inventors: Robert Edward Henry, Roseville (AU); Karthikeyan Selvarajan, Gosford (AU); Philip Rodney Kwok, Chatswood (AU); Philip John Gunning, North Rocks (AU); John David Oates, Stanhope Gardens (AU)

(73) Assignee: Resmed Limited, Bella Vista, New South Wales (AU)

( * ) Notice: Subject to any disclaimer, the term of this patent is extended or adjusted under 35 U.S.C. 154(b) by 994 days.

(21) Appl. No.: 13/032,178

(22) Filed: Feb. 22, 2011

(65) Prior Publication Data

US 2011/0139154 A1    Jun. 16, 2011

Related U.S. Application Data

(63) Continuation of application No. 11/642,963, filed on Dec. 21, 2006, now Pat. No. 7,913,689.

(30) Foreign Application Priority Data

Dec. 21, 2005 (AU) .............................. 2005907200

(51) Int. Cl.
*A61M 11/00* (2006.01)
*A61M 16/00* (2006.01)

(52) U.S. Cl.
CPC ....... *A61M 16/00* (2013.01); *A61M 2205/3561* (2013.01); *A61M 2205/3584* (2013.01); *A61M 2205/6018* (2013.01); *A61M 2205/6054* (2013.01)

USPC ................................. 128/204.21; 128/204.18

(58) Field of Classification Search
USPC .......................... 128/204.21, 204.18, 204.23
See application file for complete search history.

(56) References Cited

U.S. PATENT DOCUMENTS

| | | | |
|---|---|---|---|
| 4,695,955 A | 9/1987 | Faisandier |
| 4,768,496 A | 9/1988 | Kreizman et al. |
| 4,944,310 A | 7/1990 | Sullivan |
| 5,413,097 A | 5/1995 | Birenheide et al. |
| 5,660,567 A | 8/1997 | Nierlich et al. |
| 5,813,404 A | 9/1998 | Devlin et al. |
| 5,950,621 A | 9/1999 | Klockseth et al. |
| 6,035,851 A | 3/2000 | Wallen |

(Continued)

FOREIGN PATENT DOCUMENTS

| | | |
|---|---|---|
| DE | 4020522 | 1/1992 |
| EP | 1 516 641 | 3/2005 |

(Continued)

OTHER PUBLICATIONS

International Search Report for PCT/AU2006/001169 mailed Nov. 29, 2006.

(Continued)

*Primary Examiner* — Steven Douglas
(74) *Attorney, Agent, or Firm* — Nixon & Vanderhye, P.C.

(57) ABSTRACT

Components of a CPAP or other patient ventilation apparatus have a remotely-readable identification tag encoded with component identification data. The flow generator controller is programmed to receive data derived from the identification tag from a tag reader, and to adapt functions of the flow controller to coordinate with the component.

11 Claims, 6 Drawing Sheets

(56) References Cited

U.S. PATENT DOCUMENTS

| | | | |
|---|---|---|---|
| 6,126,610 | A | 10/2000 | Rich et al. |
| 6,142,949 | A | 11/2000 | Ubby |
| 6,158,430 | A | 12/2000 | Pfeiffer et al. |
| 6,186,140 | B1 | 2/2001 | Hoague |
| 6,910,483 | B2 | 6/2005 | Daly et al. |
| 7,148,806 | B2 | 12/2006 | Anttila et al. |
| RE40,365 | E | 6/2008 | Kirchgeorg et al. |
| 7,424,889 | B2 | 9/2008 | Mashak |
| 7,469,698 | B1 | 12/2008 | Childers et al. |
| 7,527,053 | B2 | 5/2009 | Devries et al. |
| 7,607,437 | B2 | 10/2009 | Boyle et al. |
| 7,891,353 | B2 | 2/2011 | Chalvignac |
| 7,913,689 | B2 * | 3/2011 | Henry et al. ............. 128/204.21 |
| 7,987,847 | B2 | 8/2011 | Wickham et al. |
| 7,997,885 | B2 | 8/2011 | Allum |
| 8,006,691 | B2 | 8/2011 | Kenyon et al. |
| 8,210,173 | B2 | 7/2012 | Vandine |
| 8,210,178 | B2 | 7/2012 | Schermeier |
| 8,267,084 | B2 | 9/2012 | Kwok |
| 8,381,725 | B2 | 2/2013 | Chalvignac |
| 2001/0017134 | A1 | 8/2001 | Bahr |
| 2002/0144682 | A1 | 10/2002 | Kruger et al. |
| 2002/0174867 | A1 | 11/2002 | Gunaratnam |
| 2003/0154981 | A1 | 8/2003 | Spruiell |
| 2003/0196662 | A1 | 10/2003 | Ging et al. |
| 2004/0074495 | A1 | 4/2004 | Wickham |
| 2004/0163647 | A1 | 8/2004 | Figley et al. |
| 2004/0171982 | A1 | 9/2004 | Danchin |
| 2004/0182386 | A1 | 9/2004 | Meier |
| 2004/0210151 | A1 | 10/2004 | Tsukashima et al. |
| 2004/0226566 | A1 | 11/2004 | Gunaratnam et al. |
| 2005/0061318 | A1 | 3/2005 | Faram |
| 2005/0211761 | A1 | 9/2005 | Anttila et al. |
| 2006/0231092 | A1 | 10/2006 | Mashak |
| 2006/0278220 | A1 | 12/2006 | Schermeier et al. |
| 2007/0000491 | A1 | 1/2007 | Chalvignac |
| 2007/0144519 | A1 | 6/2007 | Henry et al. |
| 2008/0078387 | A1 | 4/2008 | Vandine |
| 2010/0147301 | A1 | 6/2010 | Kwok |
| 2010/0236552 | A1 | 9/2010 | Kwok et al. |
| 2011/0139153 | A1 | 6/2011 | Chalvignac |
| 2012/0318266 | A1 | 12/2012 | Chou |

FOREIGN PATENT DOCUMENTS

| | | |
|---|---|---|
| EP | 1 579 884 | 9/2005 |
| JP | H04-158856 | 6/1992 |
| JP | 2002-172170 | 6/2002 |
| JP | 2003-061977 | 3/2003 |
| JP | 2004-532666 | 10/2004 |
| WO | 02-053217 | 7/2002 |
| WO | 2004/060443 | 7/2004 |
| WO | 2004-112873 | 12/2004 |
| WO | WO 2005/002655 | 1/2005 |
| WO | 2005-067520 | 7/2005 |
| WO | 2006/125252 | 11/2006 |
| WO | 2007-059810 | 3/2007 |

OTHER PUBLICATIONS

Japanese Office Action issued in JP 2006-344662 issued on Nov. 22, 2011 with English Language Translation.
Kwok, U.S. Appl. No. 60/656,880, filed Mar. 1, 2005.
Kwok, U.S. Appl. No. 60/707,950, filed Aug. 15, 2006.
Examiner's First Report issued in related Australian Appln. No. 2006220222 (Nov. 8, 2010).
International Search Report for PCT/AU2006/000238 mailed Apr. 26, 2006.
Office Action issued Japanese Application No. 2007-557276 (May 10, 2011) w/English translation.
Office Action issued European Application No. 06704913.0 (Oct. 20, 2011).
Office Action for European Application No. 06126895.9, mailed Oct. 29, 2012.
Office Action for U.S. Appl. No. 13/588,556, mailed Jan. 4, 2013.
Office Action for U.S. Appl. No. 13/588,556, mailed Apr. 15, 2013.
Office Action for U.S. Appl. No. 13/588,556, mailed Nov. 22, 2013.
Supplementary Partial European Search Report for EP 06704913 mailed Oct. 20, 2011.
International Preliminary Report on Patentability for PCT/AU2006/000238 mailed Sep. 11, 2007.
Written Opinion for PCT/AU2006/000238 mailed Apr. 20, 2006.

* cited by examiner

IDENTIFICATION SYSTEM AND METHOD FOR MASK AND VENTILATOR COMPONENTS

CROSS REFERENCE TO PRIORITY APPLICATION

This application is a Continuation application of application Ser. No. 11/642,963, filed Dec. 21, 2006 and claims the benefit of Australian Application No. 2005907200, filed Dec. 21, 2005, each of which is incorporated herein by reference in their entirety.

BACKGROUND OF THE INVENTION

1. Field of the Invention

The present invention relates to an apparatus that delivers breathable gas to a patient, and to methods for coordinating breathable gas delivery to ventilator system components being used.

2. Description of Related Art

Apparatus to deliver breathable gas to a patient typically includes a flow generator, an air delivery conduit, and a patient interface. Prior to use, operating parameters of the flow generator, e.g., treatment pressure, need to be manually adjusted by the patient to coordinate with the peripheral components, e.g., patient interface, being used. For example, known flow generators include a menu system that allows the patient to select the type of peripheral components being used, e.g., by brand, method of delivery, etc. Once the components are selected by the patient, the flow generator can select appropriate operating parameters of the flow generator that best coordinate with the selected components.

One limitation of the menu set up system is a lack of future mask compatibility. The flow generator is programmed on initial set up to recognise a number of mask types and to compensate for their known pressure-flow characteristics. However the flow generator does not recognise newer mask types, and these are selected by closest fit to the existing selection options.

As a result, the design of new masks and other ventilator system components is limited by the need to keep similar pressure-flow characteristics to a known mask or component type, and new technologies which have significantly different pressure-flow characteristics—or which have variability in characteristics—have not previously been able to be adopted due to non-compatibility with the flow generators.

The present invention provides improvements to known apparatus to facilitate the coordination between the flow generator and the CPAP apparatus components.

The present invention further provides methods for coordinating the flow generator and the CPAP apparatus components.

SUMMARY OF THE INVENTION

In one form, the invention provides a CPAP apparatus comprising:
  a flow generator that generates a supply of pressurized air, said flow generator including a programmable controller;
  one or more CPAP apparatus components having a remotely-readable identification tag containing identification data;
  wherein said controller includes a data input adapted to receive data derived from a remote identification tag reader which reads said identification data, and is further adapted to adjust one or more functions of the flow generator in response to said received data.

A further form of the invention provides apparatus for set-up of a CPAP treatment parameters for a patient, including:
  a CPAP apparatus according to the invention;
  a remote identification tag reader for reading the component tag; and
  a data communication path for communicating data derived from the tag to the flow generator controller.

A further form of the invention provides a method of setting up CPAP treatment parameters for a flow generator of CPAP apparatus according to the invention, including the steps of:
  transporting the flow generator to a location, said location having a remote identification tag reader for reading a remote identification tag of a CPAP apparatus component;
  reading said remote identification tag of a CPAP apparatus component for use with the flow generator;
  deriving data from said tag and communicating said data to the flow generator controller to adapt the flow generator for use with said component.

Further aspects of the invention are set out in the claims.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

Further preferred embodiments of the invention will now be described with reference to the accompanying drawings, in which.

DETAILED DESCRIPTION OF PREFERRED EMBODIMENTS

Figure 1:
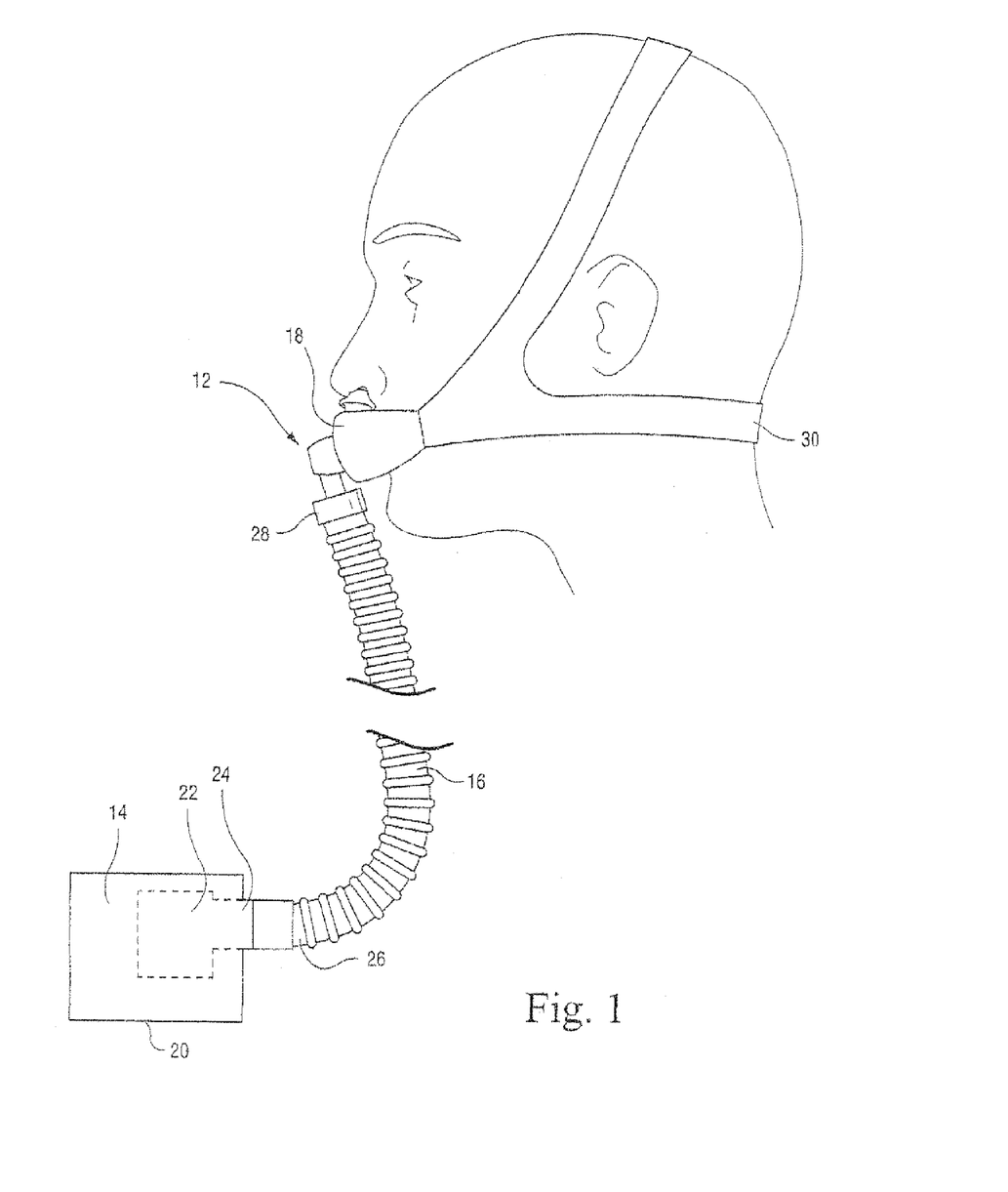
FIG. 1 is a schematic side view of an embodiment of an apparatus that delivers breathable gas to a patient.
Figure 2:
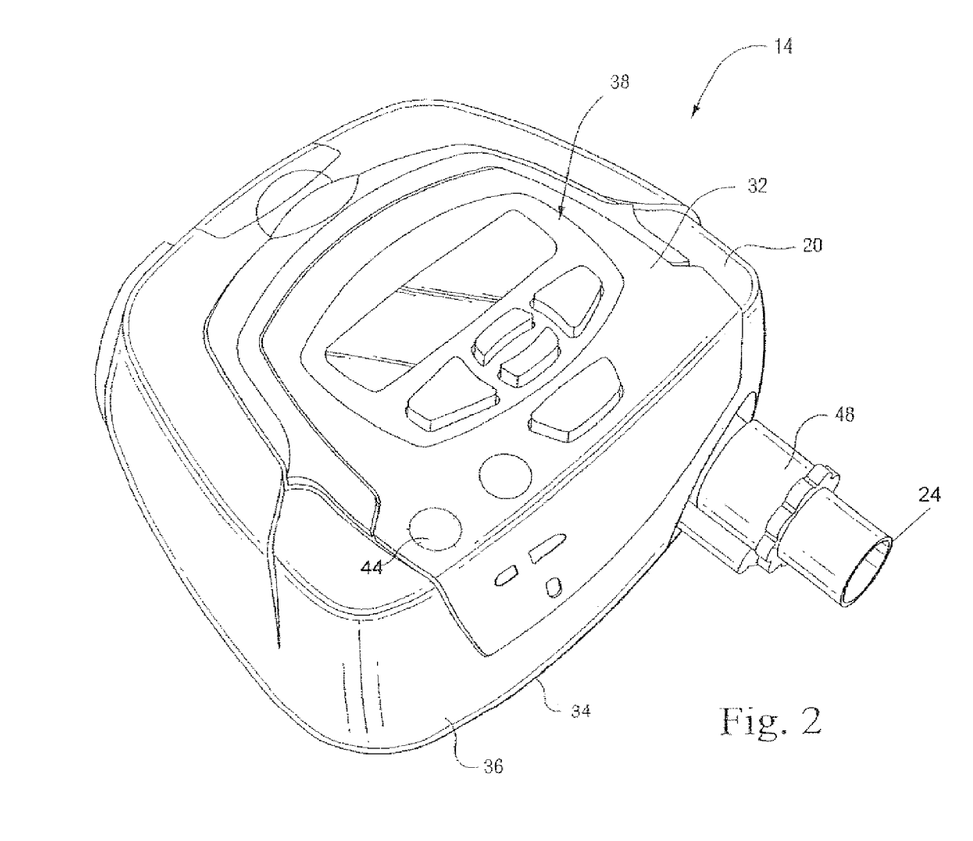
FIG. 2 is a top perspective view illustrating a flow generator.

FIGS. 1 and 2 illustrate an apparatus 12 that delivers a supply of pressurized breathable air to a patient for treatment, e.g., of Sleep Disordered Breathing (SDB) with CPAP or Non-Invasive Positive Pressure Ventilation (NIPPV). As best shown in FIG. 1, the apparatus 12 generally includes a flow generator 14, an air delivery conduit 16, and a patient interface 18.

The flow generator 14 is structured to generate a supply of pressurized air to be provided to a patient for treatment. The flow generator 14 includes a housing 20 and a blower 22 supported within the housing 20. As is known in the art, the blower 22 is operable to draw a supply of air into the housing 20 through one or more intake openings and provide a pressurized flow of air at an outlet 24.

The supply of pressurized air is delivered to the patient via the air delivery conduit 16 that includes one end 26 coupled to the outlet 24 of the flow generator 14 and an opposite end 28 coupled to the patient interface 18, as shown in FIG. 1.

The patient interface 18 comfortably engages the patient's face and provides a seal. The patient interface 18 may have any suitable configuration as is known in the art, e.g., full-face mask, nasal mask, oro-nasal mask, mouth mask, nasal prongs, etc. Also, any suitable headgear arrangement 30 may be utilized to comfortably support the patient interface 18 in a desired position on the patient's face.

FIG. 2 shows an example of a flow generator unit.

As shown in FIG. 2, the housing 20 of the flow generator 14 includes an upper wall 32, a lower wall 34, and side walls 36 that interconnect the upper and lower walls 32, 34. In the illustrated embodiment, the outlet 24 is provided in one of the side walls 36, optionally as part of a conduit connection adaptor 48. Also, the upper wall 32 incorporates a manual control unit 38 for adjusting one or more parameters of the flow generator 14, e.g., treatment pressure. However, the outlet 24 and/or control unit 38 may be incorporated into any of the walls of the housing 20. Also, it should be understood that the flow generator 14 may include additional features incorporated into the housing 20, e.g., power supply.

Figure 3:
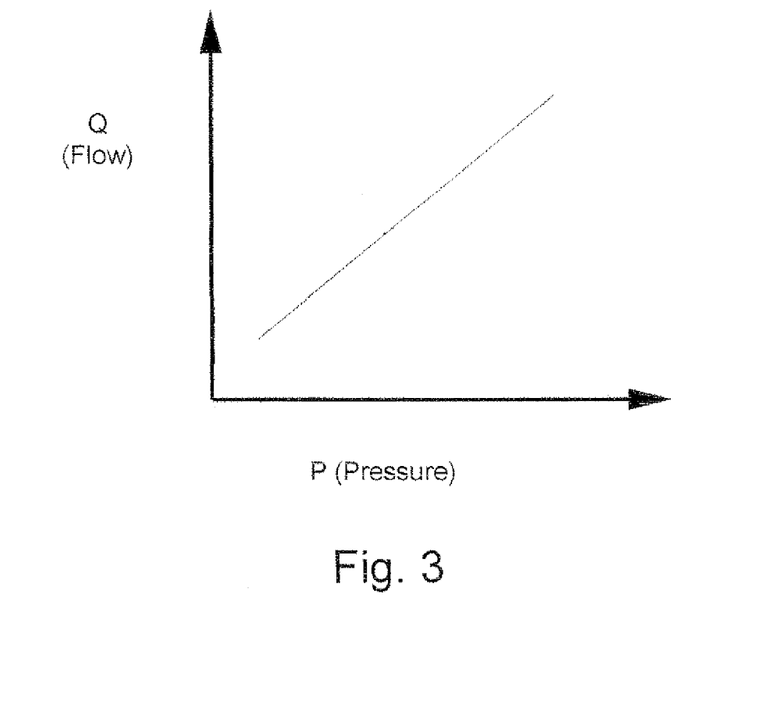
FIG. 3 is an example of a pressure-flow curve for a patient mask.

FIG. 3 shows an example of a pressure-flow curve for a patient interface, for example as may be measured in production testing of the interface.

The measured pressure-flow characteristics of interface may be stored as data in a radio frequency identification (RFID) chip incorporated in the interface. For example, the component identification data in the chip may include values for gradient and y-intercept coefficients for a line of best fit to the curve, or values of coefficients for polynomial or logarithmic approximations to the curve.

Figure 4:
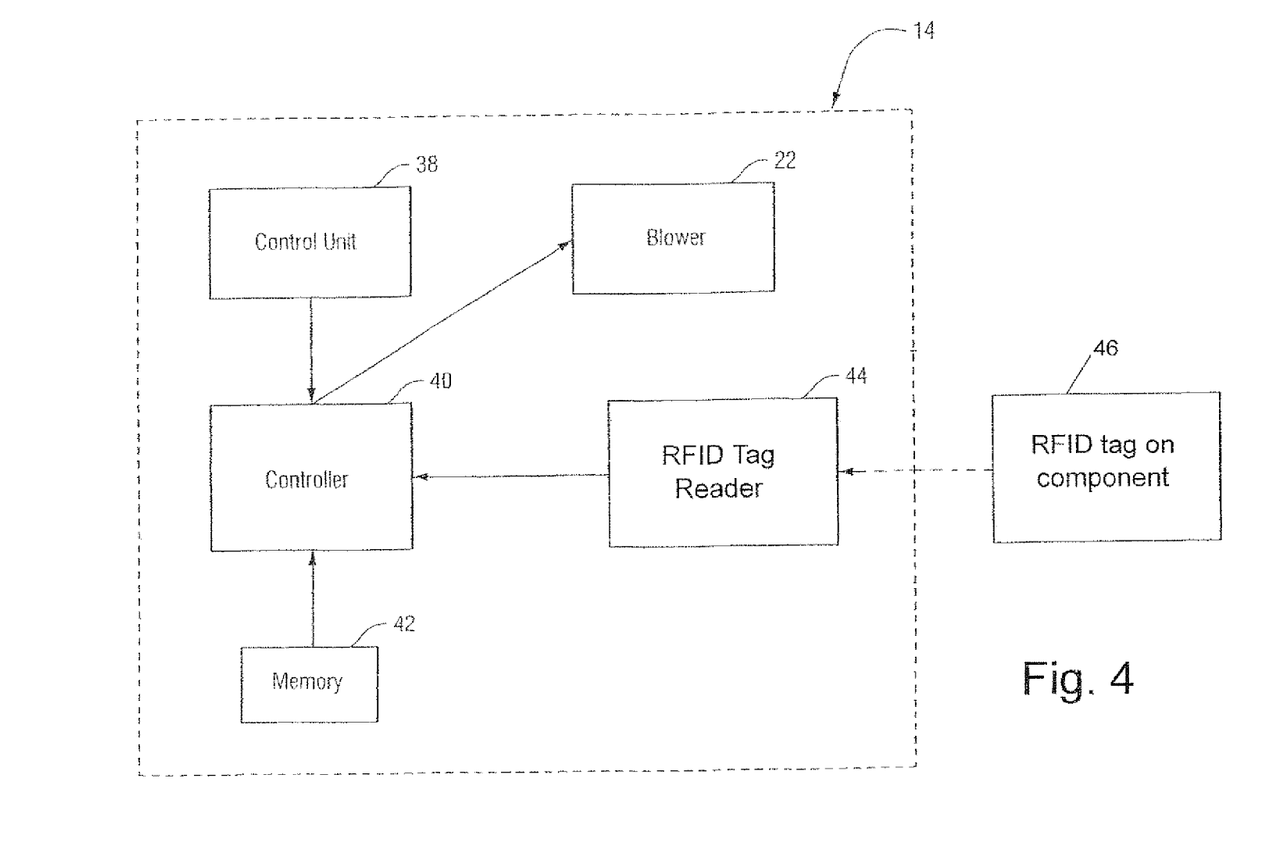
FIG. 4 is a block diagram of a flow generator set-up apparatus according to an embodiment of the invention, having an internal tag reader.

As shown schematically in FIG. 4, the flow generator 14 includes a controller 40 operable to receive input signals and to control operation of the blower 22 based on input signals. Input signals may be provided by the control unit 38 which has a plurality of control features that can be manually selected by the patient to adjust various parameters of the flow generator 14. For example, the patient may select the type of patient interface 18 being used, e.g., via a menu system of the control unit 38, from a number of known patient interface types so that the controller 40 can adjust the blower outlet pressure so that it coordinates with the selected patient interface 18. The controller 40 may include a memory 42 that stores preferred operating parameters for a variety of patient interfaces, e.g., by brand or method of delivery. When the controller 40 receives the input signal regarding the selected patient interface 18 from the control unit 38, the controller 40 can operate the blower 22 based on the stored operating parameters in the memory 42 for the selected patient interface 18. Alternatively, the preferred operating parameters for a selected patient interface 18 may be entered manually through the control unit 38.

As also shown in FIG. 4, the controller 40 of the flow generator 14 is adapted to receive data derived from remote reading of a identification tag 46 attached to or incorporated into one or more of the peripheral components, and to select appropriate operating parameters of the flow generator 14 to coordinate with the selected peripheral components.

In one embodiment, the remotely readable identification tag may be a radio frequency identification (RFID) tag, having either read-only or read-and-write capabilities depending on the type of tag reader 44 with which the tag is to be used and the functionalities desired.

The tag stores identification data for the component, including for example a unique identifier such as serial number, a batch number, component type and/or size, and optionally component performance parameters such as pressure-flow performance parameters of the component measured during post-production testing of the component.

Other types of remote-reading technologies which may be employed in the present invention include bar coding, powerless piezo, infrared, optical recognition of colour and/or shape, smartcard and EPROM (erasable programmable read-only memory). Alternatively, the component may be tagged with a code which may be entered into the flow generator control unit 38 or otherwise communicated to the processor, and then used to retrieve the detailed information from a remote database using telecommunications, for example short message service or internet protocol form via a wired or wireless modem. The database may also be located within the flow generator and may be updated with software upgrades.

The tag reader 44 may be integrated with the flow generator unit as shown in FIG. 4, for example formed on a surface of the flow generator casing (see FIG. 2), or may be separate from the flow generator and include means for communicating with the flow generator controller 40 via a USB, network, modem or other communications port in the casing.

In use, the tagged component is swiped over or otherwise placed in sufficient proximity to the tag reader 44 to allow detection of the identification data, which data is then communicated from the reader to the controller 40. The controller 40 in turn uses this data to adjust one or more functions of the flow generator.

In one embodiment of the invention, the identification data includes pressure-flow performance parameters for a component in the airflow path, such as a filter, conduit or patient interface, and the controller adjusts the pressure and/or flow characteristics of the blower in response to the data.

In another embodiment, the identification data includes identity data for a component, and the controller 40 records the flow generator operation time against the component identity to cause a warning message to be displayed on the display of the control unit 38 advising the patient to replace the component after a set operation time or a set period has elapsed.

By way of example, the controller 40 may receive and store the identity data for an antibacterial filter of the type used in CPAP or other ventilatory therapy in hospitals, and display a warning message when the filter is due for replacement. Continued use of the component after its safe usage time has elapsed may cause the controller to shut down operation of the blower.

In a further example, the controller 40 may also use the identification data to cause to be displayed on the control unit 38 display the component type, size or settings, to facilitate reordering of components or for clinician or service review.

Other flow generator functions which may be controlled in response to detection of the component identification data include:

To limit the function of the flow generator to a single session where the identification data identifies the component as being adapted only for a single use;

Where a patient data code is available in a format recognisable to the controller or in machine-readable format, to limit the use of the component to the particular patient for hygiene purposes, for example by scanning barcodes on both the patient data and on the component and preventing the flow generator from operating with that component for any other patient code;

To switch on additional functionalities of the flow generator where it is detected that the component is suitable for that functionality, or for a limited trial period where a new component is detected.

In one embodiment, discussed below with reference to FIGS. 5 and 6, tag readers are external to the flow generators and are located at clinics and at suppliers of CPAP components such as patient interfaces.

Figure 5:
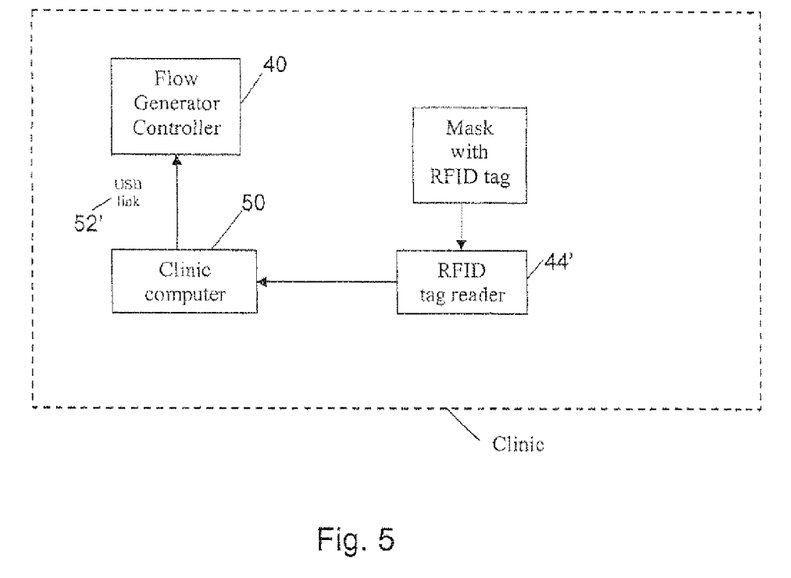
FIG. 5 is a block diagram of a further embodiment of the invention, where the tag reader is separate from the flow generator.

As shown in FIG. 5, a clinic or other central location has a tag reader 44' connected to one or more computers 50. The computer 50 has a communications link 52' such as a USB, network, wireless network or modem—for communication with the flow generator controller via a compatible communications device in the flow generator.

Figure 6:
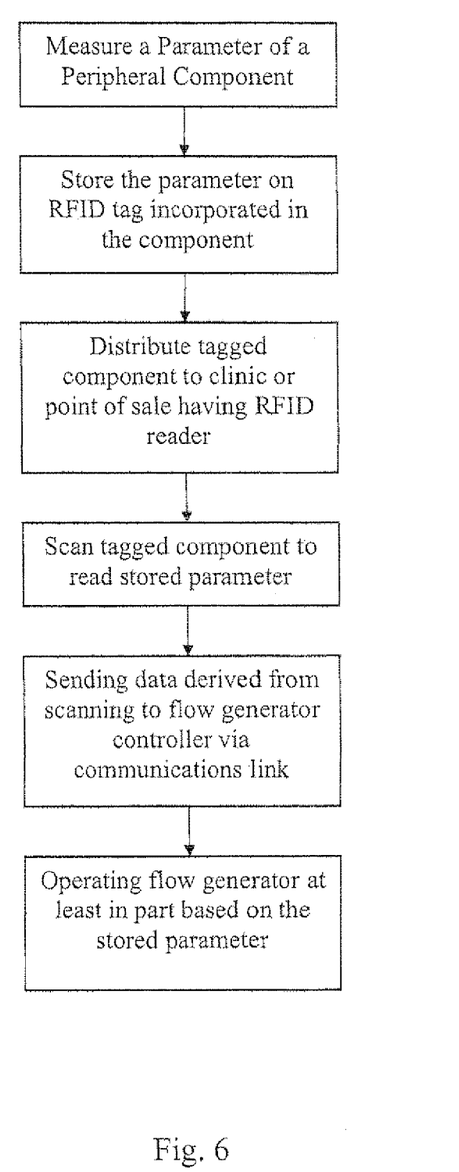
FIG. 6 is a flowchart of a method using the apparatus of FIG. 5.

As shown in FIG. 6, the performance characteristics of a component such as a patient interface are tested on the production line, and the performance parameters form part of the identification data recorded onto an REID or other readable chip which is incorporated into the component.

The patient brings the flow generator on his/her visit to the clinic. At the clinic, the clinician assesses the patient and helps the patient select the correct patient interface and other components for use with the flow generator. The clinician also determines the desired treatment settings for the patient and programs the flow generator controller to those settings. Programming of the flow generator may be done using the menu of the control unit 38 or via a communications link 52.

The tagged component is swiped past the tag reader 44', which reads the identification data from the component tag. The data is then communicated to the computer 50, which displays relevant component data on the computer display and communicates information about the component to the flow generator controller.

In the embodiment of FIG. 6, all or a selected portion of the component identification data is relayed from the computer 50 to the controller 40, with the flow generator controller programmed to receive that data and calculate adjustments for operating parameters of the flow generator to coordinate with the properties of the component.

In an alternative embodiment, the computer 50 is programmed to process the component identification data received from the tag reader to derive instructions sent to the controller 40 for adjustment of the flow generator operating parameters.

In a further alternative embodiment, a CPAP apparatus component such as a patient interface has a readable/writable tag which is capable of storing data written to it from the flow generator. The data to be written to the component tag may include treatment history data indicative of treatment performance and efficacy and patient compliance, to be uploaded to the patient interface either regularly or prior to a patient visit to the clinic. In this way, the patient may simply take the mask or other patient interface with him or her on a visit to the clinician, instead of needing to take the much larger and heavier flow generator. The clinician may then interrogate the treatment history data in the mask tag via a tag reader at the clinic, and after review the patient's treatment may write back to the tag with instructions for ongoing treatment. On return from the clinic, or prior to the next treatment session, these instructions may then be downloaded to the flow generator via its tag reader and the programming of the flow generator settings adjusted accordingly.

In a yet further embodiment, the component forms part of an airflow pathway comprising a humidifier, conduit and the patient interface, and the component identification may comprise a remote identification as discussed above or physical or other connection, for example by magnetic reed switch or other means as discussed in U.S. patent application Nos. 60/656,880 filed 1 Mar. 2005 (Kwok) and 60/707,950 filed 15 Aug. 2005 (Kwok, Gregory, Selvarajan), the contents of which are incorporated herein by reference.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein. It will further be understood that any reference herein to known prior art does not, unless the contrary indication appears, constitute an admission that such prior art is commonly known by those skilled in the art to which the invention relates.

The invention claimed is:

1. A method of setting up therapy parameters for use with a breathable pressurized gas delivery system that is configured to interface with at least one airway of a patient, breathable pressurized gas delivery system that includes a pressurized breathable gas generator and a CPAP peripheral component that has a storage device disposed thereon or therein, the method comprising:
   receiving data that is stored in the storage device of the CPAP peripheral component of the breathable pressurized gas delivery system;
   developing treatment parameters based on the retrieved data; and
   writing treatment instructions to the storage device based on the developed treatment parameters,
   wherein the treatment instructions are configured to set at least one therapy related parameter of the pressurized breathable gas system,
   wherein the CPAP peripheral component is a component in an airflow path from the breathable pressurized gas delivery system to the at least one airway of the patient.

2. The method of claim 1, wherein the received data includes treatment history data indicative of treatment performance for the patient, treatment efficacy data, and/or patient compliance data.

3. The method of claim 1, wherein the pressurized breathable gas generator is a flow generator and the treatment instructions include instructions for adjusting at least one setting on the flow generator.

4. The method of claim 3, wherein the at least one setting includes a pressure and/or flow setting of the flow generator.

5. The method of claim 1, wherein the CPAP peripheral component of the breathable pressurized gas delivery system includes a patient interface that is structured to interface with the at least one airway of the patient.

6. An CPAP apparatus comprising:
   a CPAP peripheral component that is structured to interact with a breathable pressurized gas delivery system that is configured to deliver a supply of breathable gas to at least one airway of a patient; and
   a storage medium that is disposed on or in the CPAP peripheral component, the storage medium configured to be writable by at least the breathable pressurized gas delivery system, wherein data written to the storage medium from the breathable pressurized gas delivery system includes data on a history of the delivery of the supply of breathable gas to the patient, wherein the CPAP peripheral component is a component in an airflow path from the breathable pressurized gas delivery system to the at least one airway of the patient.

7. The CPAP apparatus of claim 6, wherein the data on the history of the delivery of the supply of breathable gas includes at least one of treatment history data, treatment efficacy data, patient compliance data, and/or a therapy related parameter related to operation of the breathable pressurized gas delivery system.

8. The CPAP apparatus of claim 7, wherein the therapy related parameter related to operation of the breathable pressurized gas delivery system includes pressure and/or flow information of operation of a flow generator that is included in the breathable pressurized gas delivery system.

9. The CPAP apparatus of claim 6, wherein the CPAP peripheral component is a patient interface.

10. The CPAP apparatus of claim 6, wherein the storage medium is a writable/readable tag.

11. The method of claim 1, wherein the received data includes data related to prior use of the breathable pressurized gas delivery system by the patient.

* * * * *